United States Patent
Sato

(10) Patent No.: US 7,157,583 B2
(45) Date of Patent: Jan. 2, 2007

(54) PROCESS FOR PRODUCING HIGH-PURITY 2,3-PYRIDINEDICARBOXYLIC ACID

(75) Inventor: Toshio Sato, Kashima (JP)

(73) Assignees: Sumikin Air Water Chemical Inc., Tokyo (JP); Hebei Sinochem Fuheng Co., Ltd., Hebei (CN)

( * ) Notice: Subject to any disclaimer, the term of this patent is extended or adjusted under 35 U.S.C. 154(b) by 222 days.

(21) Appl. No.: 10/631,669

(22) Filed: Jul. 31, 2003

(65) Prior Publication Data

US 2005/0085643 A1 Apr. 21, 2005

(30) Foreign Application Priority Data

Nov. 7, 2002 (JP) ............................. 2002-323941

(51) Int. Cl.
*C07D 213/80* (2006.01)
(52) U.S. Cl. ...................................... 546/319; 546/321
(58) Field of Classification Search ................ 546/419, 546/421, 319, 321
See application file for complete search history.

(56) References Cited

U.S. PATENT DOCUMENTS

| 4,537,971 | A | * | 8/1985 | Rebhahn et al. ............. 546/320 |
| 4,754,039 | A | * | 6/1988 | Michalowicz ................ 546/320 |
| 5,959,116 | A | * | 9/1999 | Hamprecht et al. .......... 546/310 |
| 6,900,330 | B1 | * | 5/2005 | Sato et al. .................... 546/320 |

FOREIGN PATENT DOCUMENTS

| JP | 49-55673 | 5/1974 |
| JP | 56-026878 | 3/1981 |
| JP | 58-105964 | 6/1983 |
| JP | 61-212563 | 9/1986 |
| JP | 62-18551 | 4/1987 |
| JP | 62-209063 | 9/1987 |
| JP | 02-083370 | 3/1990 |
| JP | 03-271275 | 3/1991 |
| JP | 03-101661 | 4/1991 |
| JP | 03-157371 | 5/1991 |
| JP | 03-287576 | 12/1991 |

OTHER PUBLICATIONS

C. O'Murchu, Ozonolysis Of Quinolines: A Versatile Synthesis Of Polyfunctional Pyridines, Synthesis, *11*, Jul. 3, 1989, pp. 880-882.
Walter Stix Und S.A. Bulgatsch: Eine Neue Darstellungs-Art Der ChinolinsÅure, Chem. Ber. *65* 11 (1932).
Mittheilung Aus Dem Chem. Laborat. Der Akademie Der Wissensch, In Müchen, W. Koenigs: Oxydation Des Cinchonichinolins Mittelst Kaliumpermanganat, Chem. Ber. *12*, 983. (1879).

* cited by examiner

Primary Examiner—Thomas McKenzie
Assistant Examiner—Raymond Covington
(74) Attorney, Agent, or Firm—The Webb Law Firm

(57) ABSTRACT

A process for producing 2,3-pyridinedicarboxylic acid having a significantly decreased heavy metal content and capable of satisfying the purity level required for medicinal and agricultural chemicals comprising the steps of: adding at least one sulfur-containing substance selected from a hydrosulfide, a sulfide, a polysulfide, and sulfur to an aqueous solution of 2,3-pyridinedicarboxylic acid or its salt; removing the resulting precipitates from the solution; acidifying the solution with a mineral acid to precipitate 2,3-pyridinedicarboxylic acid; and recovering the precipitates. The aqueous solution to be treated may be an aqueous solution of an alkali metal salt of 2,3-pyridinedicarboxylic acid obtained by alkali decomposition of 2,3-pyridinedicarboxylic acid copper (II) salt, which has been formed or precipitated in a process for producing 2,3-pyridinedicarboxylic acid.

5 Claims, No Drawings

PROCESS FOR PRODUCING HIGH-PURITY 2,3-PYRIDINEDICARBOXYLIC ACID

FIELD OF THE INVENTION

The present invention relates to a process for producing high-purity 2,3-pyridinedicarboxylic acid having a significantly decreased heavy metal content, and particularly to a process capable of producing 2,3-pyridinedicarboxylic acid having a significantly decreased copper content when a copper compound is used in the production of 2,3-pyridinedicarboxylic acid.

DESCRIPTION OF THE RELATED ART 2,3-Pyridinedicarboxylic acid, which is also called quinolinic acid, has a wide variety of uses as intermediates in the production of medicinal or agricultural chemicals, dyes, pigments, and the like.

A number of methods have been investigated with respect to the production of 2,3-pyridinedicarboxylic acid. There have been proposed, for example, a method in which quinoline is oxidized in sulfuric acid with hydrogen peroxide or sodium chlorate in the presence of a ruthenium compound as a catalyst (JP-A 03-271275), a method in which quinoline or 8-hydroxyquinoline is oxidized with hypochlorite ions in the presence of a ruthenium compound as a catalyst (JP-A 61-212563, JP-A 02-83370, and JP-A 03-101661), a method in which quinoline is oxidized with chlorite ions in the presence of a ruthenium compound as a catalyst (JP-A 03-157371), a method in which quinoline is oxidized with oxygen in the presence of a large amount of cobalt ions (JP-A 49-55673), a method in which 8-hydroxyquinoline is oxidized with chlorate ions in the presence of vanadium ions (JP-A 58-105964), a method in which quinoline is oxidized with sodium chlorate under acidic conditions in the presence of an equimolar amount of a copper (II) salt (JP-A 62-209063), a method in which quinoline is oxidized in two steps using a chlorate salt in the final oxidation step (JP-B 62-18551), and a method in which quinoline is oxidized with chlorine dioxide generated by a reaction of methanol and a chlorate salt (JP-A 03-287576).

Additional known methods for the production of 2,3-pyridinedicarboxylic acid include a method in which quinoline is oxidized with hydrogen peroxide in the presence of copper (II) ions [Chem. Ber. 65, 11 (1932), JP-B 60-54305], a method in which 8-hydroxyquinoline is oxidized with nitric acid [Chem. Ber. 12, 983 (1879)], and a method in which quinoline is oxidized with ozone [Synthesis, 11, 880 (1989)].

Among the above-listed Japanese patent applications, JP-A 61-212563 discloses that a solution of a crude 2,3-pyridinedicarboxylic acid obtained by oxidation of quinoline is treated at pH of about 1 by addition of copper (II) sulfate to cause the 2,3-pyridinedicarboxylic acid to precipitate as its copper (II) salt, which is separated and dispersed in water. Hydrogen sulfide gas is then passed through the resulting dispersion of the copper (II) salt at about 60° C. to decompose the copper (II) salt and recover a purified 2,3-pyridinedicarboxylic acid. JP-A 03-101661 and JP-B 60-54305 also disclose that 2,3-pyridinedicarboxylic acid copper (II) salt can be readily decomposed by treatment with hydrogen sulfide or sodium hydroxide (or generally a caustic alkali) to form 2,3-pyridinedicarboxylic acid.

However, a method of producing 2,3-pyridinedicarboxylic acid from its copper (II) salt by treatment with hydrogen sulfide or other sulfide is of no commercial value for the following reasons.

(1) The treatment requires a large excess amount of hydrogen sulfide or other sulfide. As a result, the purified 2,3-pyridinedicarboxylic acid is contaminated with sulfur or thionic acid, which not only produces an unpleasant odor but deteriorates the quality of the product. It is described in JP-B 60-54305 that the quinolinic acid produced by the method disclosed therein is yellow and its purity is only 91%.

(2) The treatment involves the precipitation of copper (II) sulfide as a by-product in an equimolar amount, and it is difficult or takes a long period of time to separate the precipitated by-product.

(3) It is difficult to find applications for reuse of the copper (II) sulfide which is formed as a by-product in a large amount. From a commercial or economic viewpoint, it is practically impossible to reuse the copper (II) sulfide by-product. In contrast, when the decomposition of copper (II) salt is performed by treatment with an aqueous solution of a caustic alkali, copper (II) oxide is formed as a by-product, and it is readily soluble in an acid to form a copper (II) salt, which can be recycled in a process of producing 2,3-pyridinedicarboxylic acid.

Among the various methods for producing 2,3-pyridinedicarboxylic acid by an oxidation reaction as described above, a method in which the oxidation reaction is carried out with a chlorate salt in the presence of copper (II) ions is advantageous in view of the amount of the reactant required and the productivity.

The present inventors found that a 2,3-pyridinedicarboxylic acid product having a significantly decreased amount of organic impurities can be obtained once the resulting acid is precipitated as its copper (II) salt during the oxidation reaction or a subsequent purification or separation step. This is presumed to be attributable to the nature of copper (II) ions that can selectively form an insoluble salt with 2,3-pyridinedicarboxylic acid compared to the starting material and by-products.

The compound 2,3-pyridinedicarboxylic acid is mainly used for agricultural and medicinal chemical applications, and such applications strictly restrict the content of heavy metals. Generally, therefore, these chemicals are required to have a heavy metal content of less than 25 mg/kg as determined in accordance with the heavy metal test, the second method specified in Japanese Pharmacopeia. However, use of a copper (II) compound in the oxidation reaction to produce 2,3-pyridinedicarboxylic acid or in the precipitation of the product as its copper (II) salt for separation or purification inevitably causes the product to be contaminated by copper (II), and the product generally has a copper content of 50–500 mg/kg and more typically of 100–300 mg/kg.

A chemical plant used in industry is normally made of a metallic material such as stainless steel. In this case, iron and other heavy metals may be dissolved out of the plant or containers to contaminate the product, thereby further increasing the heavy metal content of the product.

In the conventional production of 2,3-pyridinedicarboxylic acid for use in the field of medicinal and agricultural chemicals, it was necessary to use high-purity reactants having a low heavy metal content and a chemical plant or production equipment made of a non-metallic material in order to prevent the resulting product from being contaminated by heavy metals, and this requirement raised the production costs of 2,3-pyridinedicarboxylic acid.

It is known that removal of heavy metals, particularly copper, from 2,3-pyridinedicarboxylic acid is extremely difficult, and this difficulty is the main cause of the fact that the use or presence of a copper (II) compound is disliked or excluded from commercial-scale production of 2,3-pyridinedicarboxylic acid (see JP-A 03-271275, JP-A 02-83370, JP-A 03-157371, JP-A 58-105964, and JP-B 62-18551).

Thus, there is a need in the art to develop a technique capable of readily removing heavy metals from 2,3-pyridinedicarboxylic acid with a low cost, the heavy metals coming from the reactants or other agents used in the production process or from the plant or other equipment.

SUMMARY OF THE INVENTION

The present invention provides a process for producing high-purity 2,3-pyridinedicarboxylic acid having a decreased heavy metal content by developing a technique capable of readily removing heavy metals from 2,3-pyridinedicarboxylic acid, thereby making it possible to produce 2,3-pyridinedicarboxylic acid of a purity satisfying the requirements for use in the agricultural and medicinal applications with low costs.

The present inventors found that a solution of 2,3-pyridinedicarboxylic acid or its soluble salt can be readily freed of heavy metals by precipitating heavy metals in the form of their sulfides. Thereafter, a high-purity 2,3-pyridinedicarboxylic acid having a significantly decreased heavy metal content can be recovered from the solution by acidifying the solution to precipitate 2,3-pyridinedicarboxylic acid.

Thus, the present invention provides a process for producing 2,3-pyridinedicarboxylic acid having a decreased heavy metal content comprising the steps of: adding at least one sulfur-containing substance selected from hydrosulfides, sulfides, polysulfides, and sulfur to a solution of 2,3-pyridinedicarboxylic acid or a salt thereof; removing the resulting precipitates from the solution; acidifying the solution with a mineral acid to precipitate 2,3-pyridinedicarboxylic acid; and recovering the precipitates.

DESCRIPTION OF THE PREFERRED EMBODIMENT

In a preferred embodiment of the invention, the solution of 2,3-pyridinedicarboxylic acid or its salt is obtained by a process of producing 2,3-pyridinedicarboxylic acid in which a copper (II) compound is used in at least one step in the process. More preferably, the solution is an aqueous solution of an alkali metal salt of 2,3-pyridinedicarboxylic acid obtained by alkali decomposition of copper (II) 2,3-pyridinedicarboxylate.

The raw material which is treated by a process according to the present invention is a solution of 2,3-pyridinedicarboxylic acid or its salt. The solvent of the solution may be any solvent capable of dissolving 2,3-pyridinedicarboxylic acid or its salt. Although an organic solvent such as dimethylformamide (DMF) may be used, generally it is preferable that the solvent be water. A mixed solvent of water with a water-miscible organic solvent such as an alcohol or ketone may be used. In the following description, the present invention will be described with respect to the case where the solution is aqueous, but it should be noted that the solution may be non-aqueous.

The aqueous solution of 2,3-pyridinedicarboxylic acid or its salt may be prepared in any manner. The solution may be formed by dissolving 2,3-pyridinedicarboxylic acid or its salt prepared by a suitable method in water, or it may be an aqueous solution of a 2,3-pyridinedicarboxylic acid salt which is obtained as an intermediate product in a process for producing 2,3-pyridinedicarboxylic acid.

When the solvent is water, the solubility of free 2,3-pyridinedicarboxylic acid in water is not very high, so it is advantageous to dissolve the 2,3-pyridinedicarboxylic acid in the presence of a suitable cation so as to form an aqueous solution of its soluble salt, since it becomes possible to form an aqueous solution having an increased concentration. The soluble salt is preferably either an alkali metal salt such as sodium salt or potassium salt or ammonium salt.

The process according to the present invention is particularly effective when it is applied to an aqueous solution of 2,3-pyridinedicarboxylic acid or its salt which has been obtained as a product or intermediate in a process for producing 2,3-pyridinedicarboxylic acid in which a copper (II) compound is used. A typical example of such an aqueous solution is an aqueous solution of an alkali metal salt of 2,3-pyridinedicarboxylic acid obtained by alkali decomposition of copper (II) 2,3-pyridinedicarboxylate in water.

The process for producing 2,3-pyridinedicarboxylic acid in which a copper (II) compound is used includes (A) a process in which a starting material such as quinoline or 8-hydroxyquinoline is oxidized in the presence of copper (II) ions whereby copper (II) 2,3-pyridinedicarboxylate is precipitated as an intermediate, and (B) a process in which an aqueous solution of 2,3-pyridinedicarboxylic acid or its soluble salt formed as a product is treated for separation or purification with a copper (II) compound so as to precipitate copper (II) 2,3-pyridinedicarboxylate, which is substantially insoluble in water.

Examples of process (A) which involves an oxidation reaction in the presence of copper (II) ions are described in JP-A 62-209063, JP-B 60-54305, and Chem. Ber. 65, 11 (1932). An example of process (B) in which 2,3-pyridinedicarboxylic acid is separated by precipitation of copper (II) 2,3-pyridinedicarboxylate is described in JP-A 61-212563.

In each of processes (A) and (B), the resulting precipitates of copper (II) 2,3-pyridinedicarboxylate are separated by filtration, for example, and the copper (II) salt is decomposed in water by reacting with a caustic alkali or sulfide. An aqueous solution of 2,3-pyridinedicarboxylic acid in its alkali metal salt form or free acid form is then obtained by removing precipitates (of copper (II) oxide or sulfide) formed as a by-product in the decomposition reaction. To the aqueous solution obtained in this manner, it is possible to apply a process according to the present invention. Thus, a sulfur-containing substance is added to the solution to remove heavy metal contaminants as precipitates, and the purified solution is then acidified with a mineral acid and, if necessary, concentrated, thereby making it possible to recover purified 2,3-pyridinedicarboxylic acid as a solid product.

It should be noted that even if the aqueous solution is obtained by decomposing the copper (II) salt of 2,3-pyridinedicarboxylic acid by a reaction with a sulfide, the resulting solution of 2,3-pyridinedicarboxylic acid is not completely freed of copper (II), so the resulting product has an undesirably high copper content (see JP-B 62-18551). In contrast, according to the present invention, copper (II) and other heavy metals can be effectively removed by treating the aqueous solution with a sulfide.

A particularly preferable example of process (A) in which an oxidation reaction to form 2,3-pyridinedicarboxylic acid is performed in the presence of copper (II) ions is described in JP-A 62-209063. In this process, quinoline is oxidized with a chlorate salt in an acidic medium in the presence of copper (II) ions to form a reaction mixture in which copper (II) 2,3-pyridinedicarboxylate is precipitated as an intermediate product. The copper (II) salt is isolated from the reaction mixture and then reacted with a caustic alkali (e.g., sodium hydroxide) in water in order to decompose the copper (II) salt with precipitating copper (II) oxide as a by-product. After removal of the copper (II) oxide precipitates, an aqueous solution of an alkali metal salt of 2,3-pyridinedicarboxylic acid is obtained. The aqueous solution is then acidified by addition of a mineral acid, thereby causing the resulting 2,3-pyridinedicarboxylic acid to precipitate to recover it as a solid product.

Thus, in this process, the oxidation of quinoline in the presence of copper (II) ions leads to the formation of copper (II) 2,3-pyridinedicarboxylate as an intermediate product, which is then subjected to alkali decomposition and subsequent acidification to precipitate and recover the desired 2,3-pyridinedicarboxylic acid product. When copper (II) 2,3-pyridinedicarboxylate is formed by a different oxidation method or it is precipitated from 2,3-pyridinedicarboxylic acid for the purpose of separation thereof, it can be treated in the same manner by alkali decomposition and subsequent acidification to obtain 2,3-pyridinedicarboxylic acid.

In accordance with the present invention, an aqueous solution of an alkali metal salt of 2,3-pyridinedicarboxylic acid obtained in the alkali decomposition stage in the above-described process can be purified so as to be freed of heavy metals by applying a process of the present invention to the solution. Thus, the purification is performed by adding a sulfide or similar sulfur-containing substance to the aqueous solution and removing the resulting precipitates. It has been found that this purification can remove heavy metals from an aqueous solution of 2,3-pyridinedicarboxylic acid or its salt with a significantly higher efficiency compared to a conventional method such as treatment with an ion-exchange resin so that the subsequent acidification of the purified solution to precipitate 2,3-pyridinedicarboxylic acid makes it possible to obtain a product having a significantly decreased heavy metal content.

As described earlier, the aqueous solution to be purified is not limited to one obtained from a copper (II) salt of 2,3-pyridinedicarboxylic acid by alkali decomposition. Even in the case of 2,3-pyridinedicarboxylic acid or its salt which has been formed as a product or intermediate by a process in which no copper (II) compound is used, it contains an appreciable amount of heavy metals which come from the reactants or other agents or equipment used in the process. By applying a process of the present invention to an aqueous solution of such 2,3-pyridinedicarboxylic acid or its salt (which, if its solubility in water is not sufficient, may be converted to an alkali metal salt, for example, in water), it becomes possible to obtain 2,3-pyridinedicarboxylic acid having a significantly decreased heavy metal content.

In a process according to the present invention, one or more sulfur-containing substances selected from hydrosulfides, sulfides, polysulfides, and sulfur are added to an aqueous solution of 2,3-pyridinedicarboxylic acid or its salt, thereby causing heavy metal ions present in the solution to precipitate as insoluble sulfides. The precipitates are removed by a suitable technique such as filtration, leaving an aqueous solution having a significantly decreased heavy metal content.

Examples of hydrosulfides, sulfides, and polysulfides which can be used in the present invention include hydrogen sulfide, sodium hydrosulfide, potassium hydrosulfide, and ammonium hydrosulfide for hydrosulfides; sodium sulfide, potassium sulfide, calcium sulfide, and ammonium sulfide for sulfides; and sodium polysulfide, potassium polysulfide, and ammonium polysulfide for polysulfides.

Sulfur can be used when the aqueous solution is alkaline. In this case, sulfur reacts with hydroxide ions in the solution to form sulfide or polysulfide ions, which are effective to precipitate heavy metal ions. Thus, the sulfur-containing substance which is used in the present invention may be any substance which produces hydrosulfide, sulfide, or polysulfide ions in the aqueous solution, i.e., it may be any precursor of these ions.

The amount of the sulfur-containing substance which is added is desirably at least equivalent to the heavy metal ions present in the aqueous solution, and it is usually in the range of from 1 to 10 equivalents and preferably from 1.5 to 5 equivalents. The reaction of heavy metal ions with the added substance proceeds even at room temperature, but the aqueous solution may be heated to a temperature up to the boiling point. Particularly, when sulfur is added, it is preferable to heat the solution. Since the amount of the sulfur-containing substance is small, it may be added in the form of an aqueous solution thereof. This treatment is preferably continued for 10 to 60 minutes with stirring. Simultaneously with this purification treatment by addition of a sulfur-containing substance or separately therefrom, the aqueous solution may be subjected to decoloring treatment using active carbon, for example.

After the resulting precipitates of heavy metal sulfides or the like are removed from the aqueous solution, the solution is acidified with a mineral acid to precipitate 2,3-pyridinedicarboxylic acid. The mineral acid may be selected from hydrochloric acid, sulfuric acid, and nitric acid, although other mineral acids may be used. If necessary or desirable, the aqueous solution may be concentrated. The precipitated 2,3-pyridinedicarboxylic acid is then separated by filtration or a similar technique to recover 2,3-pyridinedicarboxylic acid having a significantly decreased heavy metal content.

In accordance with a process according to the present invention, it is possible to recover 2,3-pyridinedicarboxylic acid having a heavy metal content of less than 25 mg/kg and preferably 10 mg/kg or less as determined in accordance with the heavy metal assay, the second method specified in the Japanese Pharmacopeia, or a copper content of less than 20 mg/kg and preferably 5 mg/kg or less determined by ICP analysis of a solution of an ashed sample dissolved in a mineral acid. In addition to copper (II), the content of iron, which tends to dissolve out from the equipment used in the commercial-scale production of a product and contaminate the product, can be decreased to the same level as copper (II).

Particularly, when 2,3-pyridinedicarboxylic acid is prepared by a process involving an oxidation reaction in the presence of copper (II) ions to precipitate the resulting 2,3-pyridinedicarboxylic acid as its copper (II) salt followed by alkali decomposition of the copper (II) salt and acidification to recover 2,3-pyridinedicarboxylic acid as precipitates, the present invention can be put into practice by simply adding the following steps to the process: adding a sulfide or the like to the aqueous solution obtained by the alkali decomposition of the copper (II) salt and removing the resulting precipitates from the solution. As a result, it is possible to recover a high-purity product in which the heavy metal impurity level is decreased to one tenth or less of its initial level.

Thus, while it is no longer necessary to use an expensive, high purity starting material or non-metallic equipment in the commercial-scale production of 2,3-pyridinedicarboxylic acid, the present invention makes it possible to produce high-purity 2,3-pyridinedicarboxylic acid with reduced costs.

EXAMPLES

The following examples are presented to further illustrate the present invention. These examples are to be considered in all respects as illustrative and not restrictive. In the examples, all percentages are % by weight unless otherwise indicated, and 2,3-pyridinedicarboxylic acid is abbreviated as 2,3-PDCA.

In the examples, the contents of iron and copper (II) were determined by the ashing-ICP method in which a sample (in solution or solid form) is ashed and the resulting ash is dissolved in a mineral acid (hydrochloric acid) and subjected to ICP analysis. The limit of detection in this ashing-ICP method was 1 mg/kg. Thus, a content which is expressed as "<1 mg/kg" indicates that the content was lower then the limit of detection. The content of heavy metals was determined in accordance with the heavy metal assay, the second method specified in the Japanese Pharmacopeia (hereinafter simply referred to as the pharmacopeia method). The limit of detection in the pharmacopeia method was 10 mg/kg.

Reference Example 1

0.2 grams of ammonium sulfide were added to 1000 grams of an aqueous 15% solution of 2,3-PDCA sodium salt which had been prepared by dissolving a commercially available, technical grade 2,3-PDCA in an aqueous sodium hydroxide solution, and after the solution was stirred for 30 minutes, the resulting precipitates were removed by filtration. The content of copper and iron in the solution which were determined by the ashing-ICP method before and after the treatment is shown below.

TABLE 1

| Heavy Metal Content of aqueous 2,3-PDCA sodium salt solution (mg/kg) | | |
| --- | --- | --- |
|  | Iron[1] | Copper[1] |
| Before Treatment | 17 | 31 |
| After Treatment | <1 | <1 |

[1]Ashing-ICP method

Example 1

100 grams of commercially available, technical grade 2,3-PDCA (99.8% purity, white) were dissolved in 600 grams of an aqueous 10% sodium hydroxide solution. To the resulting aqueous solution of 2,3-PDCA sodium salt, 0.15 grams of sodium sulfide were added, and after the solution was stirred for 30 minutes, the resulting precipitates were removed by filtration. To the filtrate, 35% hydrochloric acid was added so as to acidify the solution to pH 1, and the resulting precipitates of 2,3-PDCA were collected by filtration and dried. The yield was 94 grams (99.8% purity, white). The heavy metal content of 2,3-PDCA before and after the treatment is shown below.

TABLE 2

| Heavy Metal Content of 2,3-PDCA (solid) (mg/kg) | | | |
| --- | --- | --- | --- |
|  | Iron[1] | Copper[1] | Heavy Metals[2] |
| Before Treatment | 32 | 160 | 100 |
| After Treatment | <1 | 5 | <10 |

[1]Ashing-ICP method;
[2]Pharmacopeia method

Example 2

400 grams of 2,3-PDCA copper (II) salt which had been recovered from an aqueous 2,3-PDCA solution by adding copper (II) sulfate so as to precipitate the acid as its copper (II) salt were suspended in 1400 grams of an aqueous 15% sodium hydroxide solution and treated for 1 hour at 70° C. The resulting precipitates of copper (II) oxide were removed by filtration, and the filter cake was washed with water. The filtrate and washings were combined to obtain 1650 grams of an aqueous solution of 2,3-PDCA sodium salt. To 500 grams of this solution, 1.2 grams of sodium sulfide were added, and after the solution was stirred for 30 minutes, the resulting precipitates were removed by filtration. The filtrate was acidified to pH 1 by addition of 35% hydrochloric acid, and the precipitated 2,3-PDCA was collected by filtration and dried to recover 73 grams of a 2,3-PDCA product (99.8% purity, white) (treated product).

For comparison, the above-described procedure was repeated except that the procedures of addition of sodium sulfide and subsequent removal of the resulting precipitates were omitted, and also in this case, 73 grams of a 2,3-PDCA product (99.8% purity, white) (untreated product) were obtained.

The results of analysis of the treated and untreated products of 2,3-PDCA are shown below.

TABLE 3

| Heavy Metal Content of 2,3-PDCA (solid) (mg/kg) | | | |
| --- | --- | --- | --- |
|  | Iron[1] | Copper[1] | Heavy Metals[2] |
| Untreated Product | 31 | 211 | 120 |
| Treated Product | <1 | 5 | <10 |

[1]Ashing-ICP method;
[2]Pharmacopeia method

Example 3

Referring to an example described in JP-A 62-209063, 2,3-PDCA was prepared starting from quinoline in the following manner.

A glass flask was charged with 104.4 grams of quinoline, 810 grams of water, 202 grams of copper (II) sulfate pentahydrate, 101 grams of 98% sulfuric acid, and 304 grams of sodium chlorate and heated at 98–103° C. for 17 hours to allow the oxidation reaction of quinoline to proceed.

The resulting precipitates of 2,3-PDCA copper (II) salt were separated by filtration. The collected wet cake was mixed with 75 grams of sodium hydroxide and 450 grams of water, and the mixture was heated at 70° C. for 1 hour to subject the copper (II) salt to alkali decomposition. The copper (II) oxide which had been precipitated as a by-product was then removed by filtration with washing with water, and 700 grams of an aqueous solution of 2,3-PDCA sodium salt were obtained. The aqueous solution of the sodium salt was divided into halves.

One half (350 grams) of the aqueous solution of the sodium salt was acidified to pH 1 with 35% hydrochloric acid, and the resulting precipitates were collected by filtration and dried to give 33.6 grams of 2,3-PDCA (99.8% purity, white) as an untreated product.

To the other half (350 grams) of the aqueous solution of the sodium salt, 2 grams of sodium sulfide were added, and the solution was heated at 70° C. for 30 minutes. After the precipitated solids were removed by filtration, the filtrate was acidified to pH 1 with 35% hydrochloric acid, and the resulting precipitates were collected by filtration and dried to give 33.2 grams of 2,3-PDCA (99.8% purity, white) as a treated product.

The results of analysis of the treated and untreated products of 2,3-PDCA are shown below.

TABLE 4

Heavy Metal Content of 2,3-PDCA (solid) (mg/kg)

| | Iron[1] | Copper[1] | Heavy Metals[2] |
|---|---|---|---|
| Untreated Product | 13 | 130 | 80 |
| Treated Product | <1 | <1 | <10 |

[1]Ashing-ICP method;
[2]Pharmacopeia method

In this example, the iron content of the untreated product is relatively low compared to Example 2, since each procedure for the synthesis was carried out in a glass vessel. As a trial, iron hydroxide was added to the aqueous solution of 2,3-PDCA sodium salt in an amount sufficient to give an untreated product of 2,3-PDCA having an iron content of 200 mg/kg. The same aqueous solution of the sodium salt to which iron hydroxide had been added was treated in accordance with the present invention, and the resulting treated product of 2,3-PDCA had an iron content of 3 mg/kg. Thus, the present invention is also effective in commercial scale production of 2,3-PDCA in which contamination by iron dissolved from equipment may occur.

From the results of the above examples, it is demonstrated that treatment of an aqueous solution of 2,3-PDCA or its salt with a sulfide or similar sulfur-containing substance before acidifying the solution can effectively remove heavy metals and give 2,3-PDCA having a significantly decreased heavy metal content after acidification to precipitate 2,3-PDCA.

The invention claimed is:

1. A process for producing 2,3-pyridinedicarboxylic acid having a decreased heavy metal content, comprising the steps of:
    adding at least one sulfur-containing substance selected from hydrosulfides, sulfides, polysulfides, and sulfur to a solution of 2,3-pyridinedicarboxylic acid or a salt thereof;
    removing the resulting precipitates from the solution;
    acidifying the solution with a mineral acid to precipitate 2,3-pyridinedicarboxylic acid; and
    recovering the precipitated 2,3-pyridinedicarboxylic acid.

2. The process of claim 1 wherein the solution of 2,3-pyridinedicarboxylic acid or a salt thereof is obtained by a process of producing 2,3-pyridinedicarboxylic acid in which a copper (II) compound is used in at least one step.

3. The process of claim 2 wherein the solution is an aqueous solution of an alkali metal salt of 2,3-pyridinedicarboxylic acid obtained by alkali decomposition of copper (II) 2,3-pyridinedicarboxylate.

4. The process of claim 1 wherein the recovered 2,3-pyridinedicaboxylic acid has a heavy metal content of less than 25 mg/kg as determined in accordance with the heavy metal assay, the second method specified in the Japanese Pharmacopeia.

5. The process of claim 2 wherein the recovered 2,3-pyridinedicarboxylic acid has a copper content of less than 20 mg/kg as determined by ICP analysis of a solution of an ashed sample dissolved in a mineral acid.

* * * * *